United States Patent [19]
Hughes et al.

[11] Patent Number: 5,478,988
[45] Date of Patent: Dec. 26, 1995

[54] THERMAL EXCHANGE COMPOSITION AND ARTICLES FOR USE THEREOF

[75] Inventors: Thomas E. Hughes, Cedar Mountain, N.C.; R. Scott Sparkman, Cleveland, Ga.

[73] Assignee: Thermionics Corporation, Springfield, Ill.

[21] Appl. No.: 188,428

[22] Filed: Jan. 28, 1994

[51] Int. Cl.$^6$ ................................................. H05B 6/80
[52] U.S. Cl. .................... 219/730; 219/735; 219/759; 426/243; 165/59; 165/46; 99/DIG. 14
[58] Field of Search ................................. 219/730, 759, 219/728, 686, 735, 211; 128/403; 99/DIG. 14; 426/107, 109, 243; 165/59, 46, 61

[56] References Cited

U.S. PATENT DOCUMENTS

| | | |
|---|---|---|
| 4,253,983 | 3/1981 | Blanie . |
| 4,714,445 | 12/1987 | Templeton . |
| 4,743,726 | 5/1988 | Hughes et al. . |
| 4,849,593 | 7/1989 | Hughes et al. ............... 219/759 |
| 4,851,287 | 7/1989 | Hartsing, Jr. ............... 428/325 |
| 4,931,608 | 6/1990 | Bills ........................... 219/759 |
| 4,950,868 | 8/1990 | Moss et al. ................. 219/211 |
| 4,983,798 | 1/1991 | Eckler et al. ............... 219/759 |
| 5,070,223 | 12/1991 | Colasante ................... 219/759 |
| 5,089,186 | 2/1992 | Moore et al. ............... 264/25 |
| 5,175,031 | 12/1992 | Ochocki ..................... 219/759 |

FOREIGN PATENT DOCUMENTS

| | | |
|---|---|---|
| 1452833 | 10/1986 | U.S.S.R. . |
| 9005508 | 5/1990 | United Kingdom . |
| WO9220755 | 11/1992 | WIPO . |

Primary Examiner—Philip H. Leung
Attorney, Agent, or Firm—Dority & Manning

[57] ABSTRACT

A thermal exchange composition made from clay, glycol and/or water for retaining and slowly releasing hot and cold temperatures is provided. The composition can further include polyacrylamide, for mixing with water, and olivine. The composition can be incorporated and used in a variety of applications. For instance, the thermal exchange composition can be used in hot and cold packs for therapeutic treatment to sore areas of the body. Other articles incorporating the thermal exchange composition include food trays, stadium seats, and the like. A thermal delivery device is also provided. The thermal delivery device can be incorporated into a variety of articles, including toys and food containers.

41 Claims, 4 Drawing Sheets

THERMAL EXCHANGE COMPOSITION AND ARTICLES FOR USE THEREOF

BACKGROUND OF THE INVENTION

This invention relates generally to a thermal exchange composition and more particularly to a heat or cold retaining composition which can be incorporated into many articles including hot and cold packs, toys, seat cushions, or food trays.

Many different compositions and devices for heating or cooling surfaces or objects have been tried and used in the past in a limitless variety of applications. Particularly, many heating or cooling devices have been applied to the human body for therapeutic treatment. For instance, hot water bottles and ice packs still remain as very popular articles for application to sore areas of the body.

Recently, other heat or cold retaining compositions have been developed. These compositions are capable of absorbing, storing, and then releasing heat or cold over an extended period of time. For example, a PCT application, International Publication No. WO90/05508, to Wilkins discloses a heating pad comprising a heat retaining base material formed from gel, wax or oil, within a sealed flexible container. Heat storage mediums such as fibers, threads, or foam particles can be interspersed within the base material. Other additives could include polyurethane foam or china clay, which is also known as kaolin.

U.S. Pat. No. 4,253,983 to Blanie discloses a paraffin composition that can be used as a shapable heat casing constituent. The paraffin composition can contain finally divided metals, their oxides, or their silicates. Additionally, kaolin can be added.

U.S. Pat. Nos. 4,743,726 and 4,849,593, which were jointly invented by one of the present inventors, also disclose heat exchange mediums. The heat exchange medium in the '726 patent includes a microwave heatable outer structure made of a heat and flame resistant rubber coated with a high temperature lubricant assembled together with a water impregnable cellular core saturated with water. The whole assembly has at the longitudinal and diametrical center a wax core with a high melting point. The patent discloses a number of applications for the heat exchange medium, such as hair rollers, curling irons, food warmers, and heating pads.

The '593 patent discloses another microwave activated heating element made from a variety of compositions. In one particular form, a cartridge includes a core of wax material, a layer of open cellular water retaining material, a layer of rubber, and an outer layer of paper. In another embodiment, the cartridge consists of a central core formed of a wood dowel, an annular overlay of rubber material with an appropriate high temperature lubricant disposed therebetween, and an outer covering, for example, formed of paper. Another form disclosed in the '593 patent includes a heating element comprising clay, which can be mixed with water and oils. The mixture may also include rubber particles and a high temperature lubricant.

A soft, light weight toy for a child having an animal-like appearance and including a removable bladder filled with a heat transfer liquid is disclosed in U.S. Pat. No. 4,714,445 to Templeton. Suggested materials to fill the bladder and act as a heat reservoir include water, aqueous solutions, glycerol, mineral oils, and various other viscous fluids or gels. The fluid can be heated or cooled and the bladder can be inserted into the toy for making the toy warm or cool to the touch.

Soviet Union Patent No. 1452-833-A further discloses a composition made from crushed powdered clay and a dust or oil for protecting foundations against frost effects.

Although the prior art discloses an assortment of heat exchange mediums and corresponding applications for those mediums, the particular composition of the present invention remains absent. Further, the prior art has its drawbacks and deficiencies. For instance, some of the prior art compositions contain materials considered to be toxic or generally unsafe. Consequently, disposal of these items raises a number of environmental issues. Also, some of the prior art devices contain low viscous liquids. If the containment pouch were ruptured during use, these liquids would flow out of the container and possibly burn the user. Further, some of the prior art mediums simply do not meet the thermal requirements of some applications. The present invention overcomes the shortcomings of the prior art in that a thermal exchange composition is disclosed that effectively absorbs, stores, and releases higher and lower temperatures.

A PCT application, International Publication No. WO92/20755, directed to a heat exchange medium was filed by one of the current inventors. The particular features of the present invention, however, remain absent from the published PCT application as will be apparent to one skilled in art from the detailed description which follows. That application is incorporated herein in its entirety by reference thereto.

SUMMARY OF THE INVENTION

The present invention recognizes and addresses the foregoing disadvantages, and others of prior art constructions, and methods.

Accordingly, it is an object of the present invention to provide a thermal exchange composition capable of absorbing, retaining, and releasing warmer and colder temperatures than the ambient temperature.

It is another object of the present invention to provide a thermal exchange composition comprising a clay and propylene glycol that is capable of being heated by microwaves.

It is another object of the present invention to provide a hot and cold pack containing a thermal exchange composition sealed in a plastic pouch.

It is still another object of the present invention to provide various articles incorporating a thermal exchange composition.

It is another object of the present invention to provide a thermal delivery device for use in toys, food service products, and the like.

It is a further object of the present invention to provide a thermal exchange composition including olivine for added heat and cold retention.

These and other objects are achieved by providing a thermal exchange composition for retaining and slowly releasing hot and cold temperatures. Generally, the composition comprises a microwave reactive clay and a glycol, wherein the clay is present in the composition in an amount from about 20 percent to about 90 percent by weight and the glycol is present in the composition from about 10 percent to about 80 percent by weight. The microwave reactive clay can include such clays as fire clay, bentonite clay, or mixtures thereof. Preferably, the glycol included in the composition is propylene glycol.

The thermal exchange composition can further include a gel formed from a mixture of water and polyacrylamide. The water can be present in the composition in amount up to about 50 percent by weight. Another ingredient that can be added to the composition is olivine. The olivine can be present in the composition in an amount up to about 70 percent by weight.

In another exemplary embodiment, the thermal exchange composition of the present invention includes a microwave reactive clay being present in the composition in an amount from about 20 percent to about 90 percent by weight. Olivine and a polyacrylamide and water gel can be mixed with the clay. Water can be present in the composition in an amount up to about 80 percent by weight. Optionally, propylene glycol can be added to the composition.

Another present exemplary embodiment includes a thermal exchange composition for retaining and slowly releasing hot and cold temperatures including a microwave reactive clay, propylene glycol, and a polyacrylamide and water gel. The clay is present in the composition in an amount from about 60 percent to about 80 percent by weight. Propylene glycol is present in the composition in an amount from about 15 percent to about 35 percent by weight and water is present in an amount up to about 10 percent by weight. Further, olivine can be added to the composition. In another option, the clay is present in an amount of from about 20 percent to about 40 percent by weight, the propylene glycol is present in the composition in an amount from about 20 percent to about 40 percent by weight, and water is present in the composition in an amount of about 50 percent by weight.

The present invention is also directed to a hot and cold pack, including a sealed outer covering for completely enclosing a thermal exchange composition therein. The outer covering is made from a plastic material. The thermal exchange composition includes a microwave reactive clay and propylene glycol. The clay is present in the composition in an amount from about 20 percent to about 90 percent by weight, and the propylene glycol is present in the composition up to about 80 percent by weight. The thermal exchange composition can further include olivine and/or a gel made from a mixture of water and polyacrylamide.

The outer covering can be made from laminated layers of nylon and thermoplastic resin or polyester and thermoplastic resin. Further, wax stitches or a one-way, gas release valve can be included in the hot and cold pack for releasing gas contained within the pack during packaging or overheating. Further, the pack can be coated with a flocking material.

Another embodiment of the present invention includes a thermal delivery device for retaining and slowly releasing hot and cold temperatures. The thermal delivery device includes a tubular hot and cold pack having a heat and cold releasing surface and a sealed outer covering made from a flexible plastic material. A thermal exchange composition is contained within the outer covering. A thermal reflector is positioned adjacent to the hot and cold pack, covering an outer portion thereof for reflecting thermal diffusion out through the heat and cold releasing surface. The thermal delivery device can further include a means for allowing gas within the hot and cold pack to be released during overheating. Gas release means can include, for instance, a one-way gas release valve.

A flexible bladder can also be included in the thermal delivery device. The flexible bladder can be attached to the thermal reflector opposite the tubular hot and cold pack. The flexible bladder can include a collapsible container enclosing a fill material. A predetermined number of air vents can extend from the bladder through the thermal reflector such that when the bladder is compressed, air within the fill material is forced through the vents and out through the thermal delivery device. Optionally, the fill material can be scented or the bladder can include a gas release means for releasing excess gas from within the hot and cold pack.

The thermal delivery device can further include one or more booster cores. The booster cores can be made of ceramic materials, soapstone or olivine for increasing the thermal retention characteristics of the delivery device.

The thermal delivery device can be incorporated into many different articles, such as stuffed animals, stadium seats, or food preparation products.

Another embodiment of the thermal delivery device includes an outer box made from a thermal reflective material. The box has a vented lid covering a top end and contains multiple layers of materials with different thermal capabilities. The outer box contains a bottom layer made from a thermal insulating material and a top layer comprising a thermal exchange composition, wherein hot and cold temperatures retained within the thermal delivery device are predominantly released through the vented lid for respectively warming and cooling a surface or article in close proximity thereto.

The thermal delivery device can further include two intermediate layers. A lower intermediate layer includes a thermal exchange composition while an upper intermediate layer includes a material having different thermal capabilities than the thermal exchange composition such that the upper intermediate layer can retain heat for a longer period of time. The upper intermediate layer can be made from materials such as soapstone, ceramic, or olivine.

The thermal delivery device can further include a spacer panel located between the vented lid and the top layer for pressing the layers together when the lid is closed for improving heat transfer within the device. The spacer panel can include a cutout portion which generally corresponds to the vents located on the lid.

In either embodiment of the thermal delivery device, the thermal exchange composition can include a microwave reactive clay and propylene glycol. The clay is present in the composition in an amount from about 20 percent to about 90 percent by weight, while the propylene glycol is present in the composition in an amount up to about 80 percent by weight. The thermal exchange composition can further include olivine and/or a gel made from a mixture of water and polyacrylamide.

Those of ordinary skill in the art will better appreciate the features and aspects of such embodiments and others upon review of the remainder of the specification.

BRIEF DESCRIPTION OF THE DRAWINGS

A full and enabling disclosure of the present invention, including the best mode thereof directed to one of ordinary skill in the art, is set forth in the remainder of the specification, which makes reference to the appended figures in which.

Repeat use of reference characters in the present specification and drawings is intended to represent same or analogous features or elements of the invention.

DETAILED DESCRIPTION OF THE PREFERRED EMBODIMENTS

The present invention relates generally to a thermal exchange composition which can be incorporated into a variety of applications. The basic composition comprises a mixture of clay and a glycol, such as propylene glycol. Other ingredients can be added such as water and/or polyacrylamide. Also, olivine, a mineral, can be added for further increasing the hot and cold retention characteristics of the composition.

Preferably, the clay is present in the thermal exchange composition from about 20 percent by weight to about 90 percent by weight. The clay is also preferably microwave heatable or, in other words, microwave reactive. As used here, microwave reactive refers to a substance that will heat up or, in other words, increase in temperature when exposed to microwave radiation. Microwave reactive is opposite in meaning to microwave invisible, which, as used here, refers to a substance that will not heat up when exposed to microwave radiation. If the clay component in the thermal exchange composition of the present invention is microwave reactive, then the final composition takes on a microwave reactive character, which means that the composition can be heated in a conventional microwave oven. As such, the thermal exchange composition can be heated to application temperatures or therapeutic temperatures in a matter of minutes.

One example of a microwave reactive clay is fire clay. In the past, fire clay has been used for making fire bricks and furnace linings due to its ability to resist intense heat when hardened. Here, a soft moldable fire clay is used which is generally made from the following ingredients:

| Silica (SiO$_2$) | 55.78–64.00% |
| Alumina (Al$_2$O$_3$) | 16.00–28.34% |
| Iron Oxide (Fe$_2$O$_3$) | 1.50–7.50% |
| Titania (TiO$_2$) | 1.50–1.67% |
| Magnesia (MgO) | 0.34–1.55% |
| Calcium Oxide (CaO) | 0.18–0.22% |
| Sodium Oxide (Na$_2$O) | 0.22–0.40% |
| Potassium Oxide (K$_2$O) | 1.68–4.07% |

Another common clay which is microwave reactive and which can be incorporated into the composition of the present invention is bentonite. Bentonite is a porous clay produced by the decomposition of volcanic ash and generally has the following constituents:

| Silica (SiO$_2$) | 58.00–64.00% |
| Alumina (Al$_2$O$_3$) | 18.00–21.00% |
| Iron Oxide (Fe$_2$O$_3$) | 2.50–2.80% |
| Magnesia (MgO) | 2.50–3.20% |
| Lime | 0.10–1.00% |
| Soda | 1.50–2.70% |
| Potash | 0.20% |

Besides fire clay and bentonite, any other microwave reactive clay can be incorporated into the thermal exchange composition of the present invention. Further, microwave invisible clays can also be added to the composition. Other clays include montmorillonite, kollinite, macrite, dickite, holloysite, and illite. Also, the various types and varieties of clays can be mixed together as desired. For instance, fire clay and bentonite clay can be combined before being added to the composition. Likewise, a microwave reactive clay can be mixed with a microwave invisible clay for producing a new clay with desired characteristics.

The clay component of the thermal exchange composition is mixed with propylene glycol. Preferably, propylene glycol is present in an amount from about 10 percent by weight to about 80 percent by weight. Other glycols, such as ethylene glycol, can be used, but propylene glycol is preferred because it is non-toxic and environmentally friendly.

There are many advantages to adding glycol to the thermal exchange composition. For instance, when mixed with clay, glycol can lower the viscosity of the resulting composition as desired for the particular application. Also, many of the glycols, including propylene glycol, are a microwave reactive liquid and, therefore, enhance the ability of the thermal exchange composition to be heated in a microwave oven. Further, glycols generally have a very low freezing point, allowing the thermal exchange composition to retain its fluidity in cold applications.

Besides clay and glycol, other ingredients can be added to the thermal exchange composition. One such additive is water. Preferably, water is added in any amount up to about 75 percent by weight of the composition. Water can be used to totally replace the glycol component. Preferably, however, water is used in conjunction with propylene glycol and is present in an amount up to about 30 percent by weight. Because it is a very economical ingredient, water can be added to the composition in order to soften the clay without compromising the thermal exchange characteristics of the medium while avoiding other expensive additives.

When water is added to the thermal exchange composition, polyacrylamide is preferably mixed with the water before being added to the other ingredients. Polyacrylamide, when mixed with water, forms a gel. When the final composition is heated as described herein, the polyacrylamide prevents the water from evaporating and forming an undesired gas. Further, addition of the polyacrylamide reduces the tendency of the water and clay to separate. The polyacrylamide and water gel is more easily combined with clay than water alone.

Another ingredient that can optionally be added to the thermal exchange composition is olivine. Olivine, a mineral, is microwave invisible. However, olivine is very efficient at retaining hot and cold temperatures for an extended period of time. As such, olivine further increases the thermal retention properties of the composition. In a preferred embodiment, olivine is added to the thermal exchange composition in an amount sufficient to replace up to about 75 percent by weight of the clay or, alternatively, olivine can be present in the overall composition in an amount of up to about 70 percent by weight. Olivine can be added to the thermal exchange composition as a fine powder or as particles of any size. Further, the olivine could also be sealed within a separate package and then held in contact with the thermal exchange composition.

Although olivine is microwave invisible, once present in the thermal exchange composition of the present invention, the composition can still be effectively heated by microwave radiation. When exposed to microwaves, the other ingredients will heat up and increase in temperature. This heat will then be transferred to the olivine which can retain the heat for longer periods of time.

The thermal exchange composition of the present invention can be used in many different types of applications. For instance, the thermal exchange composition can be used for therapeutic treatment in hot and cold packs. Other articles that can incorporate the thermal exchange composition of the present invention include food trays, stadium seats, coolers, and other similar food containers. The thermal exchange composition can also be used, for instance, in a stuffed animal, making the stuffed animal hot or cold to the touch when heated or chilled. Of course, there are a limitless variety of other applications and uses for the thermal exchange composition of the present invention.

Figure 1:
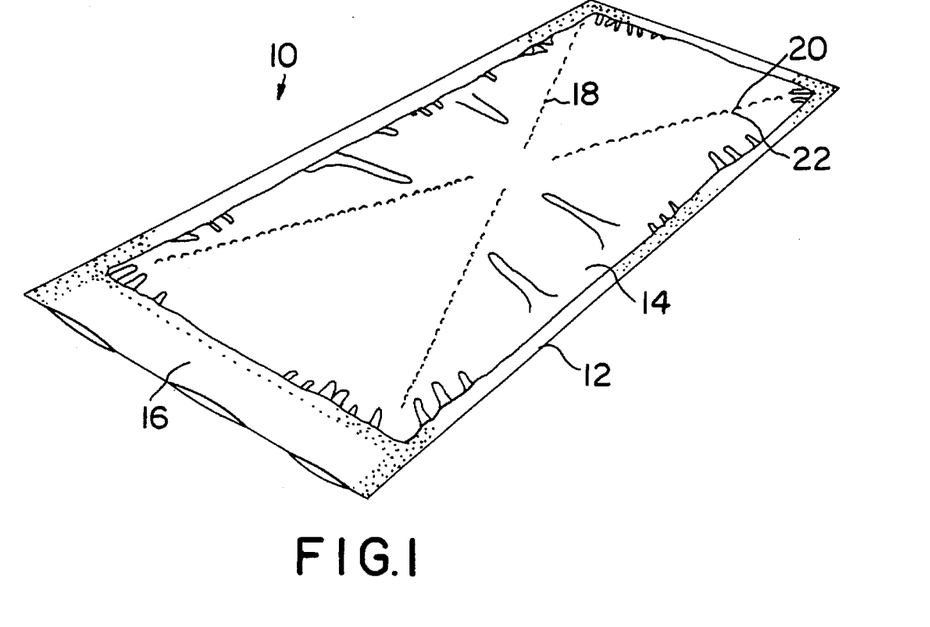
FIG. 1 is a perspective view of one embodiment of a hot and cold pack containing the thermal exchange composition of the present invention.

Referring to FIG. 1, one particular article incorporating the thermal exchange composition of the present invention is a hot and cold pack generally 10. Hot and cold pack 10 includes a plastic type covering 12 containing a thermal exchange composition 14. Hot and cold pack 10 can be heated or cooled for retaining and transferring hot and cold temperatures for therapeutic treatment or for any other desired application. When used as a hot pack, hot and cold pack 10 is preferably heated by microwave radiation. However, hot and cold pack 10 can be heated by other conventional means including gas, electricity, steam, hot water, solar, and the like. Similarly, when used as a cold pack, hot and cold pack 10 can be cooled by various cooling means including refrigeration, exposure to a cold fluid or exposure to a cold solid, such as ice. At hot and cold temperatures, hot and cold pack 10 does not harden but remains flexible for any desired application.

Referring to FIG. 1, hot and cold pack 10 can also include other optional features. For instance, hot and cold pack 10 can include a grab tab 16 made from an extended piece of plastic-like material. Grab tab 16 allows a user to easily handle hot and cold pack 10 after pack 10 has been heated or cooled. Grab tab 16 is particularly useful when hot and cold pack 10 is heated in a hot water bath. Grab tab 16 allows a user to handle hot and cold pack 10 without being burned from the hot water contained in the bath.

If hot and cold pack 10 were exposed to extremely high temperatures or to microwave radiation for an extended period of time and was subsequently overheated, thermal exchange composition 14 may produce a gas within hot and cold pack 10. In order to prevent gas buildup and to provide a means of escape for gas contained within hot and cold pack 10, pack 10 can also include a set of wax stitches 18. Wax stitches 18 include a wax thread 20 threaded in and out through a number of consecutive needle point stitches 22. Wax thread 20 can be made completely out of wax, but preferably is a wax coated thread. If hot and cold pack 10 is overheated, the wax in wax thread 20 begins to liquefy allowing any gas produced by thermal exchange composition 14 to escape through needle point stitches 22. Needle point stitches 22 are large enough to allow for the gas to escape but are too small for allowing any thermal exchange composition to leak out of hot and cold pack 10.

Wax stitches 18, as shown in FIG. 1, are generally diagonal across one side of hot and cold pack 10. Wax stitches 18, however, can be stitched into hot and cold pack 10 in any particular design, including vertical or horizontal lines. Other designs could include faces, symbols, or even printed words and names.

As stated above, hot and cold pack 10 includes outer covering 12 made from a plastic-type material. In one embodiment, the material is constructed of vinyl, or polyethylene film, one to three mils thick, bonded to nylon film of similar thickness forming laminated layers. The nylon is used in order to strengthen the material and is preferably the outer layer of the material since nylon has less effective heat sealing qualities than vinyl or polyethylene. Vinyl or polyethylene form much stronger heat sealed edges than nylon.

Nylon is also hydroscopic, meaning that it absorbs and retains water or moisture. Consequently, problems can be encountered when hot and cold pack 10 is immersed in hot water baths if the nylon is not treated. For instance, if soaked for extremely long periods of time in water, the outer nylon layer may tend to delaminate from the inner polyethylene or vinyl surface.

In order to neutralize the hydroscopic nature of nylon without compromising the strength of the material, hot and cold pack 10 can be dipped or coated with a water repellent agent such as, for example, SCOTCHGUARD sold by 3M Corporation located in St. Paul, Minn. In another embodiment, a waterproof bonding agent or adhesive can be applied in between the polyethylene or vinyl and nylon layers. Further, the water repellent agent or waterproof bonding agent can be applied only to the edges of the hot and cold pack where delamination would occur first.

In another embodiment, the material for constructing outer covering 12 of hot and cold pack 10 can include more than two laminant layers. Specifically, a layer of nylon can be sandwiched in between two layers of polyethylene or vinyl. In a preferred embodiment, the polyethylene or vinyl layers are larger and overlap the nylon layer. Consequently, the heat sealed edges of the hot and cold pack do not contain a nylon component, whereas the nylon is totally encapsulated in the other layers. The resulting material provides a barrier to water penetration incorporating the strength of nylon.

Instead of using nylon, the material used to form outer covering 12 can alternatively incorporate a layer of polyester for providing strength. The polyester can also be used in conjunction with laminate layers of vinyl or polyester. Polyester does not possess the hydroscopic characteristics of nylon and is capable of forming heat sealed edges.

In another alternative embodiment, the material used to construct the outer covering of the hot and cold pack is treated with an ultraviolet retardant in order to protect the material from ultraviolet deterioration. The ultraviolet retardant is preferably used when the material contains vinyl which is especially susceptible to deterioration when exposed to extended amounts of ultraviolet rays. The ultraviolet retardant can be applied to the material by being sprayed on, added as a layer during manufacture, or applied by dipping.

Figure 2:
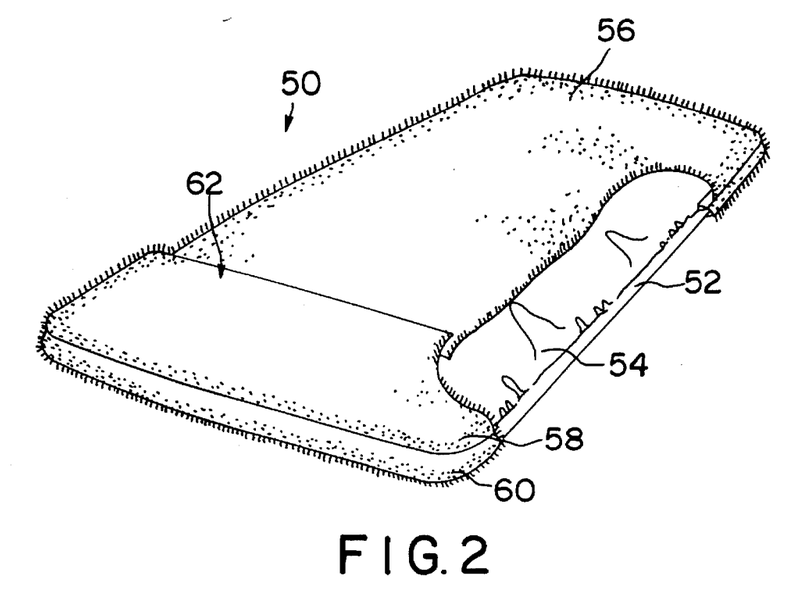
FIG. 2 is a perspective view of another embodiment of a hot and cold pack containing the thermal exchange composition of the present invention.

Referring to FIG. 2, another embodiment of a therapeutic hot and cold pack generally 50 is illustrated. Hot and cold pack 50 includes an outer covering 52 made from a plastic-like material. Contained inside outer covering 52 is a thermal exchange composition 54 made in accordance with the present invention. Hot and cold pack 50, as shown in FIG. 2, is further contained within a pouch 56 made from a soft fabric for gentle application during therapeutic treatment. Preferably, the soft fabric is felt, velour, or terry cloth. In one particular embodiment, pouch 56 includes a top side 58 and a bottom side 60. Top side 58 and bottom side 60 are made from different fabrics or from the same fabric with different thicknesses. Consequently, when in use, hot and cold pack 50 will have two sides at different temperatures allowing the user to choose the side most comfortable to the touch.

Pouch 56 can include an opening 62 for removing hot and cold pack 50. In this arrangement, pouch 56 can be washed after use. However, pouch 56 can also be permanently applied to hot and cold pack 50 by using an adhesive or other similar securing means as desired.

In another embodiment, pouch 56 can be made of a flocking material. In this embodiment, hot and cold pack 50 is sprayed or coated with an adhesive and then exposed to a flocking material for attachment thereto. As used here, flocking refers to material fibers of variable length made naturally or synthetically.

For instance, the fibers can be made from cotton, wool, polyester, or a polymer or can be woven or non-woven clothes. Preferably, an electrostatic flocking material is used for electrostatic application to the outer covering. Once applied to hot and cold pack 50, the flocking material provides space for air circulation between hot and cold pack 50 and the surface being treated. Certain flocking materials can provide moisture retention for use in moist heat therapy. Further, the flocking can be applied to hot and cold pack 50 in various colors including various designs for personalizing or for making hot and cold pack 50 aesthetically pleasing.

Figure 3:
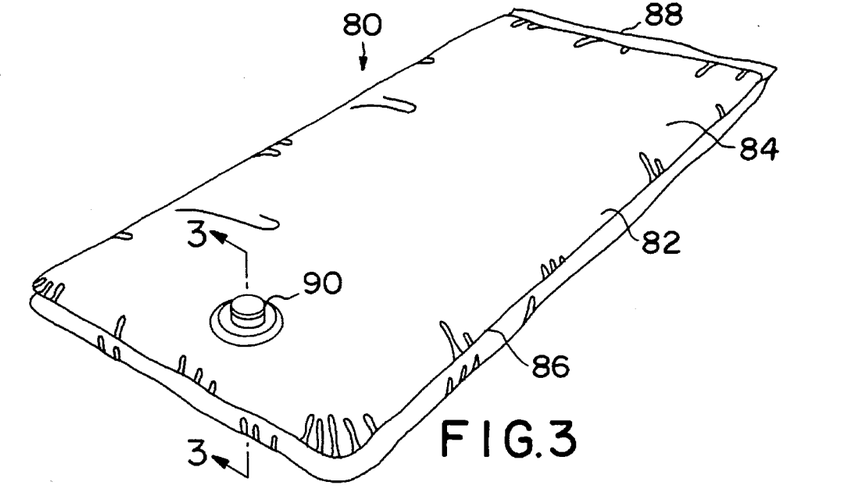
FIG. 3 is a perspective view of another embodiment of a hot and cold pack containing the thermal exchange composition of the present invention.
Figure 3A:
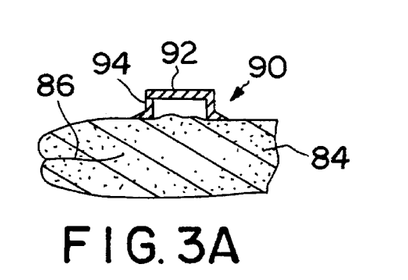
FIG. 3A is a sectional view taken along line 3—3 of FIG. 3.
Figure 3B:
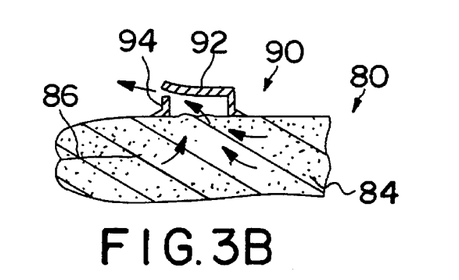
FIG. 3B is another view taken along line 3—3 of FIG. 3.

Referring to FIGS. 3, 3A, and 3B, another embodiment of a hot and cold pack generally 80 is shown. Hot and cold pack 80 includes an outer covering 82 containing a thermal exchange composition 84. In this embodiment, outer covering 82 has inverted edges 86 and a grab tab 88. By being inverted, edges 86 are stronger and can withstand greater inside pressure. Also, by using inverted edges 86, outer covering 82 can be made from an inside layer of nylon attached to an outside layer of polyethylene or vinyl. Consequently, the nylon would remain on the inside and not be exposed to water while inverted edges 86 would be made from heat sealing the outside layer of polyethylene or vinyl together. Further, by inverting edges 86, sharp edges and corners, which may have a tendency to cause discomfort to the user, are eliminated.

During manufacture, hot and cold packs can be vacuum sealed for eliminating any trapped air or gas inside the outer covering. However, vacuum sealing can be a very expensive process in terms of needed machinery and labor. Consequently, hot and cold pack 80 may include a gas release valve 90 as shown in FIGS. 3, 3A and 3B. Gas release valve 90 is preferably a one-way check valve that allows gas to escape but prevents it from entering outer covering 82.

During manufacture, hot and cold pack 80 is exposed to a roller which flattens and distributes thermal exchange composition 84 throughout outer covering 82. The rolling process forces sufficient air or gas out of hot and cold pack 80 through gas release valve 90.

As stated above, if ever overheated, thermal exchange composition 84 may have a tendency to produce unwanted gas. Gas release valve 90 also provides a means of escape for any gaseous buildup. In one particular embodiment, gas release valve 90 includes a top portion 92 as illustrated in FIG. 3A and 3B. Top portion 92 of gas release valve 90 can be secured to a bottom portion 94 by means of an adhesive. Preferably, the adhesive is either pressure or heat sensitive, meaning that the adhesive will fail under high pressure or when exposed to higher temperatures. As shown in FIG. 3B, top portion 92 will release from bottom portion 94 permitting gas to escape from hot and cold pack 80 when there is a gaseous buildup or when pack 80 is overheated. One preferred adhesive is a permanent pressure sensitive, acrylic based adhesive sold by 3M Corporation of St. Paul, Minn.

Figure 4:
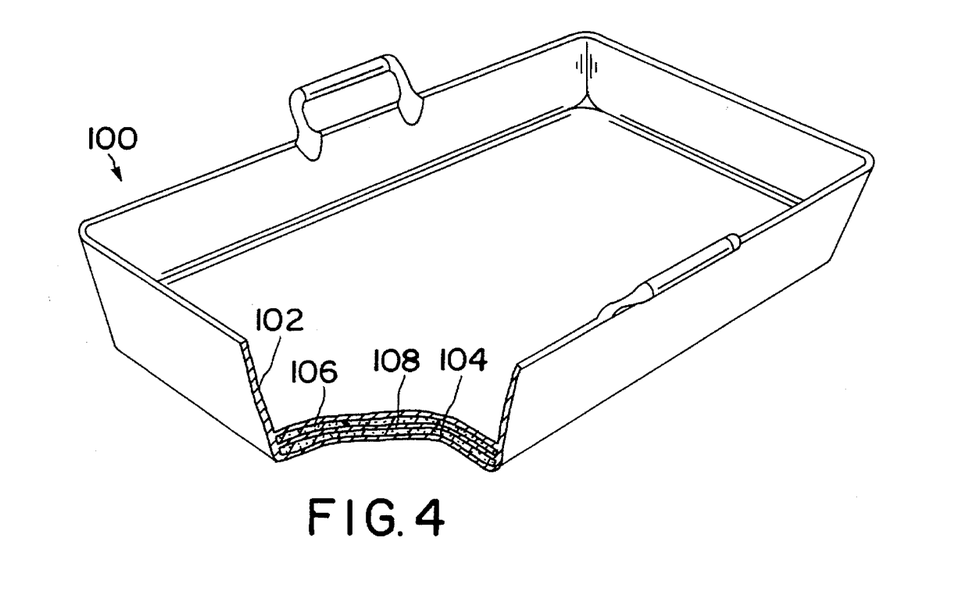
FIG. 4 is a perspective view with cutaway portions of one embodiment of a food tray made in accordance with the present invention.

As stated above, the thermal exchange composition of the present invention can be incorporated into a limitless variety of useful articles. One exemplary article, a food tray generally 100, is illustrated in FIG. 4. As shown, the bottom of food tray 100 is made from layers of different materials. Specifically, food tray 100 includes an outer base material 102 encapsulating a bottom layer 104 and a top layer 106. Bottom layer 104 is preferably made from perlite or vermiculite. Perlite and vermiculite are good insulating materials that, as shown in FIG. 4, will reflect hot or cold temperatures toward the surface of food tray 100. Layer 106 is made from the thermal exchange composition of the present invention and is capable of retaining hot and cold temperatures for application to any food items contained within food tray 100. In between layer 106 and layer 104, a middle layer 108 made from a thin plastic film is included for separating the top and bottom layers.

Depending upon the application, outer covering 102 of food tray 100 can be made from a variety of materials. For instance, if food tray 100 is to be used to keep its contents warm, outer covering 102 would be made preferably from a microwave-safe material such as plastic or ceramic. On the other hand, if food tray 100 is to be used to keep its contents cool or is only to be heated in a conventional oven, then outer covering 102 could be made of a metal, such as aluminum or stainless steel.

In other embodiments, further layers of material can be added to food tray 100. For instance, in one embodiment, food tray 100 can include four layers inside outer covering 102. One layer would, again, include perlite or vermiculite with a layer of the thermal exchange composition on top. The next layer can be made from soapstone, ceramic, or a similar material capable of absorbing and retaining hot and cold temperatures. The fourth layer can then include another layer of the thermal exchange composition. In this arrangement, the soapstone or ceramic material acts as a temperature booster for maintaining hot or cold temperatures longer once properly heated or cooled.

Figure 5:
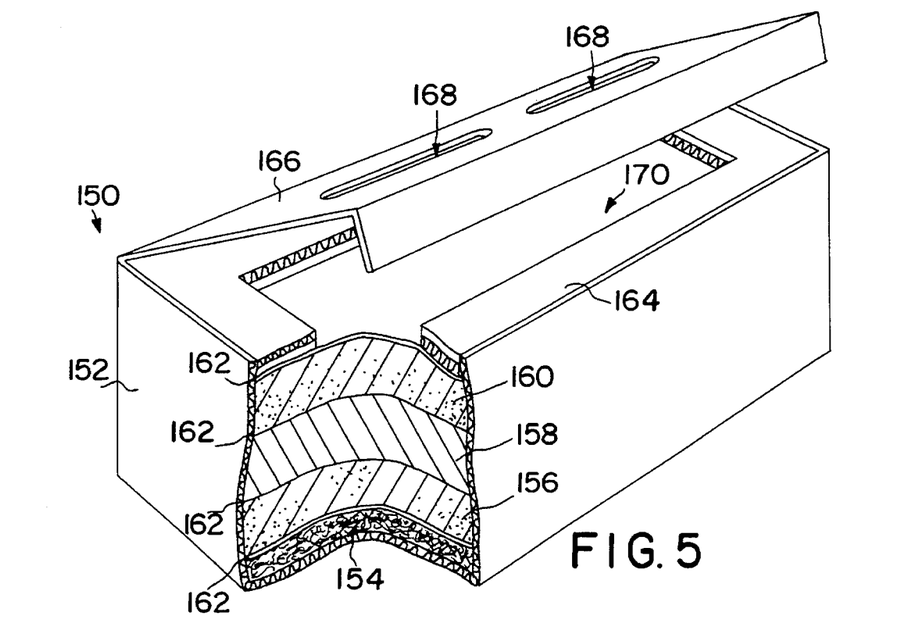
FIG. 5 is a perspective view with cutaway portions of an embodiment of a thermal delivery device made in accordance with the present invention.
Figure 6:
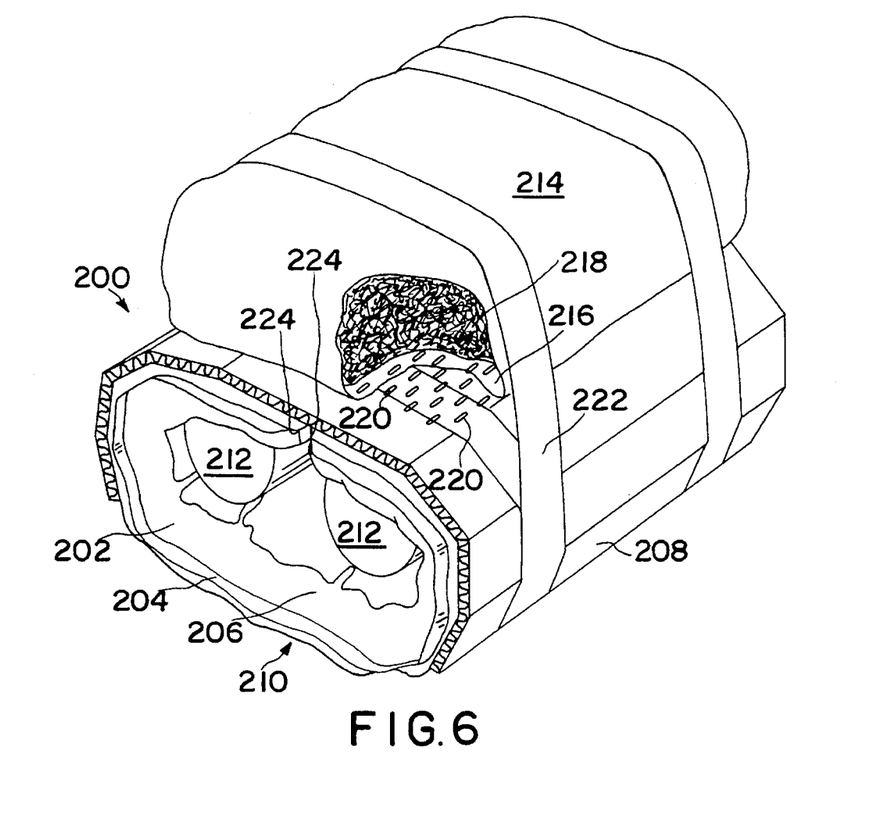
FIG. 6 is a perspective view with cutaway portions of another embodiment of a thermal delivery device made in accordance with the present invention.
Figure 7:
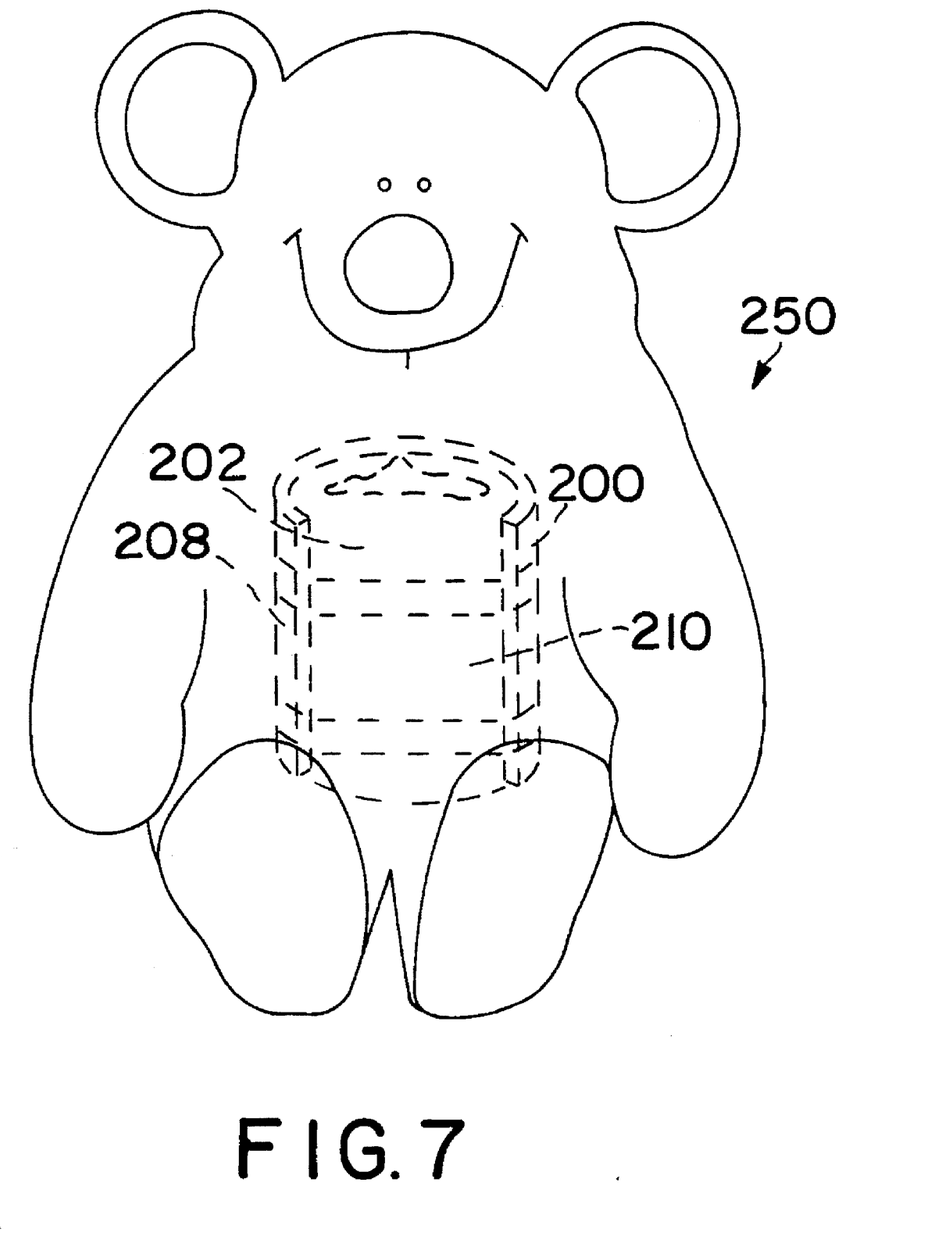
FIG. 7 is a front view of a stuffed animal containing an embodiment of a thermal delivery device made in accordance with the present invention.

Referring now to FIGS. 5 and 6, two different thermal delivery devices are illustrated. The thermal delivery devices are for incorporation into useful articles. For instance, thermal delivery devices can be used in food containers, cushions, such as stadium seats, and even stuffed animals as illustrated in FIG. 7.

A box form of a thermal delivery device generally 150 is shown in FIG. 5. Thermal delivery device 150 includes an outer box 152 containing multiple layers of material. Outer box 152 is preferably made from a thermal reflective material that is also microwave safe such as cardboard, plastic, or a metal. A bottom layer 154 is made from perlite or vermiculite. As mentioned above, perlite and vermiculite are insulating materials and, as used in thermal delivery device 150, will cause warmer or colder temperatures to reflect upwards. Consequently, the higher or lower temperatures retained within thermal delivery device 150 will not dissipate out through the bottom of device 150.

A second layer of material 156 on top of bottom layer 154 is made of the thermal exchange composition of the present invention. On top of layer 156 is a third layer 158 made from a heat or cold retaining material such as soapstone, ceramic, or olivine. A top layer 160, on top of soapstone or ceramic layer 158 is, again, made from the thermal exchange composition of the present invention.

As can be seen, soapstone or ceramic layer 158 is sandwiched between two layers of the thermal exchange composition. Soapstone and ceramic, which are effective heat or cold retaining materials, when used in conjunction with the thermal exchange composition of the present invention, increase the cold and heat retention times of the entire device. The surrounding layers of the thermal exchange composition act as insulators to preserve and retain the heat or cold within soapstone or ceramic layer 158 and provide for a substantially slower dissipation of the heat or cold from thermal delivery device 150.

Thermal delivery device layers 154, 156, 158, and 160 are separated by a thin layer 162 of plastic or wax. Thin layer 162 prevents the layers from mixing together. Thin layer 162, if made of plastic, can totally encapsulate thermal exchange composition layers 156 and 160 if desired.

Outer box 152 includes a lid 166 which can be closed and sealed over the multiple layers. A spacer or panel 164 is positioned between lid 166 and top layer 160. Spacer 164 is generally a rectangular member shaped to fit inside of box 152 and defines a centrally located cutout portion 170. Spacer 164 is made with a certain thickness so that when lid 166 is closed over box 152, spacer 164 is pushed down exerting a pressure on the multiple layers causing them to press together. The pressure caused by spacer 164 ensures that the multiple layers will remain in close contact with each other for improving heat transfer within thermal delivery device 150.

Lid 166 further includes multiple vents 168 generally aligned with cutout portion 170. Cutout portion 170 and vents 168 create a path of least resistance for the transfer of heat and cold out of outer box 152. In other words, when thermal delivery device 150 is in use, most of the heat or cold retained within the multiple layers will radiate up through vents 168 for warming or cooling a surface or an object in close proximity thereto.

Another embodiment of a thermal delivery device is illustrated in FIG. 6 generally at 200. Thermal delivery device 200 includes a hot and cold pack 202 having an outer covering 204 containing the thermal exchange composition 206 of the present invention. Hot and cold pack 202 is rolled forming a tubular member within thermal delivery device 200. Connected to and surrounding one side of hot and cold pack 202 is a thermal reflector 208. Thermal reflector 208 which can be made of cardboard, plastic, metal or other similar material causes the higher or lower temperatures contained within thermal exchange composition 206 to be substantially released out a single surface 210 of thermal delivery device 200. Thermal reflector 208 can be attached to hot and cold pack 202 by adhesive, tape, or any other similar means.

Thermal delivery device 200 can optionally include one or more booster cores 212 made of soapstone or ceramic as similarly described above. Booster core 212 is preferably made from a material that effectively retains cold and heat. Hot and cold pack 202 serves as an insulator to preserve and retain the heat or cold within booster core 212 and to provide for substantially slower dissipation of the heat or cold from thermal delivery device 200.

As shown in FIG. 6, thermal delivery device 200 can also optionally include a flexible bladder 214. Flexible bladder 214 includes a flexible film covering 216 containing fill material 218 inside. Flexible film covering 216 is preferably made from a durable plastic or paper material. Fill material 218 is made from a material that will retain and absorb air. In a preferred embodiment, fill material 218 includes a nonwoven polyester which can be scented with a desired fragrance.

Bladder 214 is attached to thermal reflector 208 by tape 222 as shown in FIG. 6. Of course, adhesive or any other similar securing means can be used. Multiple vents 220 are located between bladder 214 and reflector 208 and extend through film covering 216 and thermal reflector 208. In this arrangement, when thermal delivery device 200 is squeezed, bladder 214 is compressed forcing air through multiple vents 220 into the middle of thermal delivery device 200. The air is subsequently warmed or cooled and released out the sides of thermal delivery device 200. As such, warm or cool air is forced out through the article in which thermal delivery device is contained. As stated above, fill material 218 can further be scented which would cause scented air to be released when device 200 is squeezed.

Thermal delivery device 200 can further include vents or holes 224 for releasing gas in case hot and cold pack 202 is overheated. As shown in FIG. 6, the corners of hot and cold pack 202 have been clipped in order to form holes 224. Holes 224 are large enough to allow gas to be released but are small enough to retain thermal exchange composition 206, which is a high viscosity material. A strip of gauze or wool (not shown in FIG. 6) can be placed over holes 224 to ensure that the thermal exchange composition will not be released.

Another method for releasing excess gas from thermal delivery device 200 is for vents 220 to extend from bladder 214, through thermal reflector 208, and into hot and cold pack 202. Any excess gas buildup would, therefore, flow into and be absorbed by bladder 214. Further, bladder 214 can include additional vents in film covering 216 where the film covering is not adjacent to thermal reflector 208. These added vents would allow gas to escape from bladder 214 and thereafter be absorbed by the article in which thermal delivery device 200 is incorporated.

Thermal delivery device 200 can be incorporated into a limitless variety of applications. In FIG. 7, one particular application for thermal delivery device 200 is illustrated. As shown, a stuffed animal generally 250 contains thermal delivery device 200. Specifically, thermal delivery device 200 is contained within the stomach area of stuffed animal 250 and is arranged so that heat and cold dissipating surface 210 releases warm or cold temperatures out through the front of stuffed animal 250. In this figure, thermal delivery device 200 includes hot and cold pack 202 attached to thermal reflector 208.

From this arrangement, thermal delivery device 200 can be heated or cooled for transferring hot or cold temperatures through the cover of stuffed animal 250, making the toy warm or cool to the touch. Thermal delivery device 200 can be permanently encased within stuffed animal 250 or can be removable therefrom.

The present invention may be better understood by reference to the following examples and described embodiments.

EXAMPLE 1

One embodiment of the thermal exchange composition of the present invention is made from the following ingredients:

| Ingredient | Weight Percent |
| --- | --- |
| Water | 38% |
| Polyacrylamide | 0.5 to 3% |
| Propylene Glycol | 29% |
| Fire Clay, 200 mesh | 32% |

First, the water and polyacrylamide are mixed together thoroughly to form a gel. The gel is then mixed with propylene glycol and then added to the clay. The resulting heat exchange composition is microwave reactive and exhibits a broad range of temperature storage capabilities.

In order to demonstrate the thermal retention characteristics of the above thermal exchange composition, hot and cold tests were performed on a 1.5 pound sample, vacuum sealed in a plastic pack. The cold test was conducted by freezing the pack to −9° F. for 12 hours. The pack was then laid flat on one layer of terry cloth in a room at a temperature of 75° F. A temperature thermocouple was placed over the top of the pack. Temperatures were then monitored over time.

In the heat test, the pack was heated for four minutes at 100 percent power in a 600 watt microwave oven. The pack was then again laid flat on one layer of terry cloth in a room at a temperature of 75°. A thermocouple was placed in the center of the pack and, again, temperature measurements were taken. The following results were obtained:

TABLE 1

| Time (min) | Cold Test Temp (°F.) | Heat Test Temp (°F.) |
| --- | --- | --- |
| Initial | 15 | 162 |
| 20 | 16 | 149 |
| 40 | 16 | 137 |
| 60 | 17 | 124 |
| 80 | 19 | 116 |
| 100 | 20 | 110 |
| 120 | 22 | 103 |
| 140 | 27 | — |

EXAMPLE 2

Another preferred embodiment of the thermal exchange composition includes the following constituents:

| Ingredients | Weight Percent |
| --- | --- |
| Water | 4% |
| Polyacrylamide | 0.5 to 3% |
| Propylene Glycol | 25% |
| Fire Clay, 200 mesh | 70% |

The above thermal exchange composition was also tested for its heat and cold retention characteristics. A four pound sample of the thermal exchange composition was contained in a hot and cold pack and subjected to a heat test. After being heated, the temperature of the hot and cold pack was monitored in a 75° F room. The following results were obtained:

TABLE 2

| Time (min) | Heat Test Temp (°F.) |
| --- | --- |
| Initial | 163 |
| 10 | 158 |
| 20 | 158 |
| 30 | 145 |
| 40 | 138 |
| 50 | 131 |
| 60 | 124 |

A cold test was also performed and the following results obtained:

TABLE 3

| Time (min) | Cold Test Temp (°F.) |
| --- | --- |
| Initial | 37.4 |
| 5 | 42 |
| 10 | 50 |
| 20 | 54 |

EXAMPLE 3

Still another preferred embodiment includes the following ingredients:

| Ingredients | Weight Percent |
| --- | --- |
| Water | 68% |
| Polyacrylamide | 0.5 to 3% |
| Fire Clay | 32% |

The above thermal exchange composition contains a larger proportionate amount of water than other preferred embodiments. As such, this embodiment is more useful in cold treating applications. The composition freezes solid when exposed to cold temperatures and, when used, slowly increases in temperature due to a phase change from solid to liquid.

EXAMPLE 4

As stated above, up to 75 percent by weight of the clay component of the thermal exchange composition of the present invention can be replaced with olivine, a mineral. In one embodiment, the clay is replaced with 25 percent by weight olivine. The resulting composition has enhanced heat and cold retention characteristics.

A one pound sample of the thermal exchange composition as described in Example 1 was vacuum packed in a plastic covering and then wrapped around a 0.25 pound core of olivine. The hot and cold pack including the olivine was then heated in a microwave oven to 165° F. For comparison, a 1.25 pound hot and cold pack containing the composition of Example 1, but including no olivine, was also heated to 165° F. in a microwave oven. The time it took for the hot and cold packs to decrease in temperature down from 165° to 100° F. was recorded:

TABLE 3

| Sample | Time (hrs) |
| --- | --- |
| 1.25 lb pack | 3.45 |
| 1.00 lb pack with .25 lb olivine | 5.00 |

As shown above, the addition of olivine dramatically and unexpectedly improves the thermal retention characteristics of the heat exchange composition.

EXAMPLE 5

Another embodiment of the thermal exchange composition of the present invention includes the following:

| Ingredients | Weight Percent |
| --- | --- |
| Propylene Glycol | 25% |
| Fire Clay | 75% |

As shown, the above composition contains no water.

A one pound sample of the above composition was sealed in a hot and cold pack and heated to 165° F. It took 1.5 hours for the composition to decline in temperature to 100° F. when placed in a 75° F. room.

A cold test was also performed. The above sample was cooled to 0° F. and placed in a 75° F. room. It took 1.5 hours for the sample to increase in temperature to 40° F.

It will be understood that the present invention is not limited to the particularly described thermal exchange compositions but further includes various other compositions containing all or some of the mentioned ingredients. It should also be understood that the present invention is not limited to the specific compositions or processes described herein in that any composition having a formula equivalent to that described falls within the scope of the present invention. Preparation routes of the heat exchange mediums are merely exemplary so as to enable one of ordinary skill in the art to make the composition and use it as incorporated into the herein described articles. Particular features of the invention can be interchanged in whole or in part. It will also be understood that while the form of the invention shown and described herein constitutes a preferred embodiment of the invention, it is not intended to illustrate all possible forms of the invention. The words used are words of description rather than limitation. Various changes and variations may be made to the present invention without departing from the spirit and scope of the following claims.

What is claimed is:

1. A thermal delivery device for retaining and slowly releasing hot and cold temperatures, said thermal delivery device comprising: a thermal exchange composition; said composition consisting essentially of a microwave reactive clay and a glycol, said clay being present in said composition in an amount from about 20 percent to about 75 percent by weight and said glycol being present in said composition from about 25 percent to about 80 percent by weight; and means for encapsulating said thermal exchange composition for preventing the egress of said composition from said device, said encapsulating means allowing hot and cold temperatures retained within said composition to be released from said device.

2. The thermal delivery device as defined in claim 1, wherein said microwave reactive clay is selected from the group consisting of fire clay, bentonite clay, or mixtures thereof.

3. The thermal delivery device as defined in claim 1, wherein said glycol is propylene glycol.

4. The thermal delivery device as defined in claim 1, wherein said thermal exchange composition further consists of water.

5. The thermal delivery device as defined in claim 1, further comprising olivine.

6. The thermal delivery device as defined in claim 1, wherein said thermal exchange composition further consists of polyacrylamide.

7. The thermal delivery device as defined in claim 1, wherein said thermal exchange composition further consists of a water and polyacrylamide gel.

8. A thermal delivery device for retaining and slowly releasing hot and cold temperatures, said device comprising a sealed outer covering, said covering completely enclosing a thermal exchange composition therein, said outer covering being made from a plastic material, said thermal exchange composition comprising:

a) a microwave reactive clay, said clay being present in said composition in an amount from about 20 percent to about 90 percent by weight;

b) a polyacrylamide and water gel, said water portion of said gel being present in said composition in an amount up to about 75 percent by weight of said composition; and c) olivine.

9. The thermal delivery device as defined in claim 8, wherein said olivine is present in said composition in an amount up to about 70 percent by weight.

10. The thermal delivery device as defined in claim 8, wherein said clay is present in said composition in an amount from about 10 percent to about 30 percent by weight and said olivine is present in said composition in an amount from about 5 percent to about 30 percent by weight.

11. The thermal delivery device as defined in claim 8, further comprising propylene glycol.

12. A hot and cold pack comprising:

a) a sealed outer covering for completely enclosing a thermal exchange composition therein, said outer covering being made from a plastic material; and b) a thermal exchange composition enclosed within said sealed outer covering for retaining and slowly releasing hot and cold temperatures through said outer covering, said composition consisting essentially of a microwave reactive clay and propylene glycol, said clay being present in said composition in an amount from about 20 percent to about 75 percent by weight and said propylene glycol being present in said composition up to about 80 percent by weight.

13. The hot and cold pack as defined in claim 12, wherein said thermal exchange composition further comprises olivine.

14. The hot and cold pack as defined in claim 12, wherein said thermal exchange composition further includes a gel made from a mixture of water and polyacrylamide.

15. The hot and cold pack as defined in claim 12, wherein said sealed outer covering is made from a flexible material comprising laminated layers of nylon and thermoplastic resin, wherein said nylon is enclosed between two layers of said thermoplastic resin.

16. The hot and cold pack as defined in claim 12, wherein said outer covering is made from a flexible material comprising laminated layers of polyester and thermoplastic resin.

17. The hot and cold pack as defined in claim 12, wherein said sealed outer covering has inverted edges.

18. The hot and cold pack as defined in claim 12, wherein said sealed outer covering further comprises wax stitches therein for releasing gas when said hot and cold pack is overheated.

19. The hot and cold pack as defined in claim 12, wherein said sealed outer covering further includes a one-way, gas release valve for releasing gas contained with said hot and cold pack during packaging or overheating.

20. The hot and cold pack as defined in claim 12, wherein said sealed outer covering is coated with a flocking material.

21. A thermal delivery device for retaining and slowly releasing hot and cold temperatures, said thermal delivery device comprising:
   a) a tubular hot and cold pack having a heat and cold releasing surface, said pack comprising a sealed outer covering made from a flexible plastic material wherein said outer covering contains a thermal exchange composition, said thermal exchange composition consisting essentially of a microwave reactive clay and propylene glycol, said propylene glycol being present in said composition from about 30 percent to about 80 percent by weight.

22. The thermal delivery device as defined in claim 21, wherein said thermal exchange composition further comprises olivine.

23. The thermal delivery device as defined in claim 21, wherein said composition further comprises a gel made from a mixture of water and polyacrylamide.

24. The thermal delivery device as defined in claim 21 wherein said hot and cold pack further comprises means for allowing gas within said pack to be released during overheating.

25. The thermal delivery device as defined in claim 24, wherein said gas release means includes a one-way, gas release valve.

26. The thermal delivery device as defined in claim 21, further comprising a flexible bladder attached to said thermal reflector opposite said tubular hot and cold pack, said flexible bladder comprising a collapsible container enclosing a fill material therein, wherein a predetermined number of air vents extend from said bladder through said thermal reflector such that when said bladder is compressed, air within said fill material is forced through said vents and out through said thermal delivery device.

27. The thermal delivery device as defined in claim 26, wherein said fill material is scented.

28. The thermal delivery device as defined in claim 26, wherein said hot and cold pack further includes a gas release means generally corresponding with said vents for releasing excess gas from within said pack, said excess gas flowing into said bladder through said vents.

29. The thermal delivery device as defined in claim 21, further comprising a booster core contained within said device having different thermal capabilities than said thermal exchange composition such that said booster core can retain heat for a longer period of time.

30. The thermal delivery device as defined in claim 21, wherein said device is incorporated into a stuffed animal.

31. The thermal delivery device as defined in claim 21, wherein said device is incorporated into a stadium seat.

32. A thermal delivery device for retaining and slowly releasing hot and cold temperatures, said thermal delivery device comprising:
   a) an outer covering containing at least two layers of materials with different thermal capabilities;
   b) a bottom layer made from a thermal insulating material, said material being chosen from the group consisting of perlite and vermiculite; and
   c) a top layer comprising a thermal exchange composition capable of retaining and slowly releasing, hot and cold temperatures said top layer comprising a microwave reactive clay material.

33. The thermal delivery device as defined in claim 32, wherein said thermal exchange composition comprises a microwave reactive clay and propylene glycol, said clay being present in said composition in an amount from about 20 percent to about 90 percent by weight and said propylene glycol being present in said composition up to about 80 percent by weight.

34. The thermal delivery device as defined in claim 33, wherein said thermal exchange composition further comprises olivine.

35. The thermal exchange composition as defined in claim 33, wherein said thermal exchange composition further comprises a gel made from a mixture of water and polyacrylamide.

36. The thermal delivery device as defined in claim 32, further comprising two intermediate layers between said bottom layer and said top layer, said intermediate layers including a lower intermediate layer comprising said thermal exchange composition and an upper intermediate layer comprising a material having different thermal capabilities than said thermal exchange composition such that said upper intermediate layer can retain heat for a longer period of time.

37. The thermal delivery device as defined in claim 36, wherein said upper intermediate layer is made from a material selected from the group consisting of soapstone, ceramic, or olivine.

38. The thermal delivery device as defined in claim 32, wherein said device is incorporated into a food preparation product.

39. A toy figurine containing a thermal exchange composition for making said toy figurine warm or cool to the touch, said toy figurine comprising:
   a heat and cold releasing covering, said covering being in the shape of a toy figure and defining an inner cavity; and
   a hot and cold pack received within said cavity, said hot and cold pack comprising a thermal exchange composition encapsulated in a flexible container, said container preventing the egress of said composition from said cavity, said thermal exchange composition consisting essentially of a microwave reactive clay blended with a glycol, said glycol being present in said composition in an amount of at least 25 percent by weight.

40. A toy figurine as defined in claim 39, wherein said thermal exchange composition further consists of water.

41. A toy figurine as defined in claim 40, wherein said thermal exchange composition further consists of polyacrylamide.

* * * * *